(12) United States Patent
Hsieh et al.

(10) Patent No.: US 6,936,027 B2
(45) Date of Patent: Aug. 30, 2005

(54) SAFETY SYRINGE

(75) Inventors: Hsin-Po Hsieh, Chian-Hwa Hsien (TW); Chi-Zer Ho, Taipei (TW); Shih-Chun Wang, Chia-Yi (TW)

(73) Assignee: Syriteck Medical Devices Co., Ltd., Taichung (TW)

( * ) Notice: Subject to any disclaimer, the term of this patent is extended or adjusted under 35 U.S.C. 154(b) by 0 days.

(21) Appl. No.: 10/683,400

(22) Filed: Oct. 14, 2003

(65) Prior Publication Data
US 2005/0080379 A1 Apr. 14, 2005

(51) Int. Cl.⁷ .............................. A61M 5/00; A61M 5/32
(52) U.S. Cl. ..................................... 604/110; 604/195
(58) Field of Search .................... 604/110, 195, 187, 604/263, 198, 218, 220

(56) References Cited

U.S. PATENT DOCUMENTS

| | | | | |
|---|---|---|---|---|
| 4,650,468 A | * | 3/1987 | Jennings, Jr. | 604/110 |
| 4,675,005 A | * | 6/1987 | DeLuccia | 604/110 |
| 4,978,340 A | * | 12/1990 | Terrill et al. | 604/195 |
| 5,171,300 A | * | 12/1992 | Blake et al. | 604/110 |
| 5,205,824 A | * | 4/1993 | Mazur | 604/110 |
| 5,533,970 A | * | 7/1996 | Berger et al. | 604/110 |
| 5,634,903 A | * | 6/1997 | Kurose et al. | 604/110 |
| 6,117,113 A | * | 9/2000 | Novacek et al. | 604/195 |
| 6,183,464 B1 | * | 2/2001 | Sharp et al. | 604/533 |

* cited by examiner

*Primary Examiner*—Sharon Kennedy
(74) *Attorney, Agent, or Firm*—Rosenberg, Klein & Lee

(57) ABSTRACT

A safety syringe has a hollow barrel, a needle hub and a plunger. The hollow barrel has a distal end, a proximal end, a cone-shaped end formed on the proximal end with an opening. The plunger has a proximal end and a needle retractor formed on the proximal end. The needle hub with a needle is detachably mounted inside the proximal end of the hollow barrel and has an axial fitting to engage the plunger. When the safety syringe is used, the plunger connects to the needle hub and is pulled toward the distal end of the hollow barrel to draw the needle hub with the needle inside the hollow barrel to keep people from being hurt or infected by an exposed needle.

2 Claims, 6 Drawing Sheets

SAFETY SYRINGE

BACKGROUND OF THE INVENTION

1. Field of the Invention

The present invention relates to a syringe, and more particularly to a safety syringe that can safely hold a used needle and prevent the syringe from being used more than once.

2. Description of Related Art

To keep doctors, nurses or workers who deal with discarded syringes from being injured or infected by used needles, safety syringes with retractable needles have been designed such as the syringe in Taiwan Patent No. 356013. A conventional safety syringe has a hollow barrel, a plunger and a needle hub with a needle. The needle hub of the conventional safety syringe has an axial locking chamber, and the plunger has a proximal end and a protruding head. The protruding head is formed on the proximal end of the plunger. After injecting a medicine into a body, the proximal end of the plunger is pushed toward the needle hub, and the protruding end of the plunger is mounted inside the axial locking chamber in the needle hub. When a user pulls the plunger back, the needle hub will move inside the hollow barrel to protect a user from being hurt.

Because the needle hub is made of plastic and the protruding head of the plunger is made of a resilient material, the protruding head can be pressed into the axial locking chamber in the needle hub. However, when pulling the plunger with the needle hub back inside the hollow barrel, the needle hub easily separates from the plunger. To overcome the disadvantage, the axial locking chamber is made smaller to securely hold the protruding head of the plunger, but then the protruding head is hard to press into the axial locking chamber in the needle hub.

To overcome the shortcomings of conventional safety syringes, the present invention provides a safety syringe to mitigate or obviate the aforementioned problem.

SUMMARY OF THE INVENTION

The primary objective of the present invention is to provide a syringe that is safer and more convenient to use and handle than a conventional safety syringe. The safety syringe in accordance with the present invention has a hollow barrel, a needle hub and a plunger and features incorporated into these main elements to make the syringe safer and more convenient to use and handle than conventional safety syringes. The hollow barrel has a distal end, a proximal end and a cone-shaped end with an opening formed on the proximal end. The plunger has a proximal end and a needle retractor formed on the proximal end. The needle hub has a needle, is detachably mounted inside the proximal end of the hollow barrel and has an axial fitting to connect to the needle retractor on the plunger.

When the safety syringe is used, the needle retractor on the plunger connects to the axial fitting on the needle hub, and the plunger pulls the needle hub with the needle inside the hollow barrel when the plunger is pulled toward the distal end of the hollow barrel. With the needle completely and securely inside the hollow barrel, people cannot be hurt or infected by an exposed needle.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
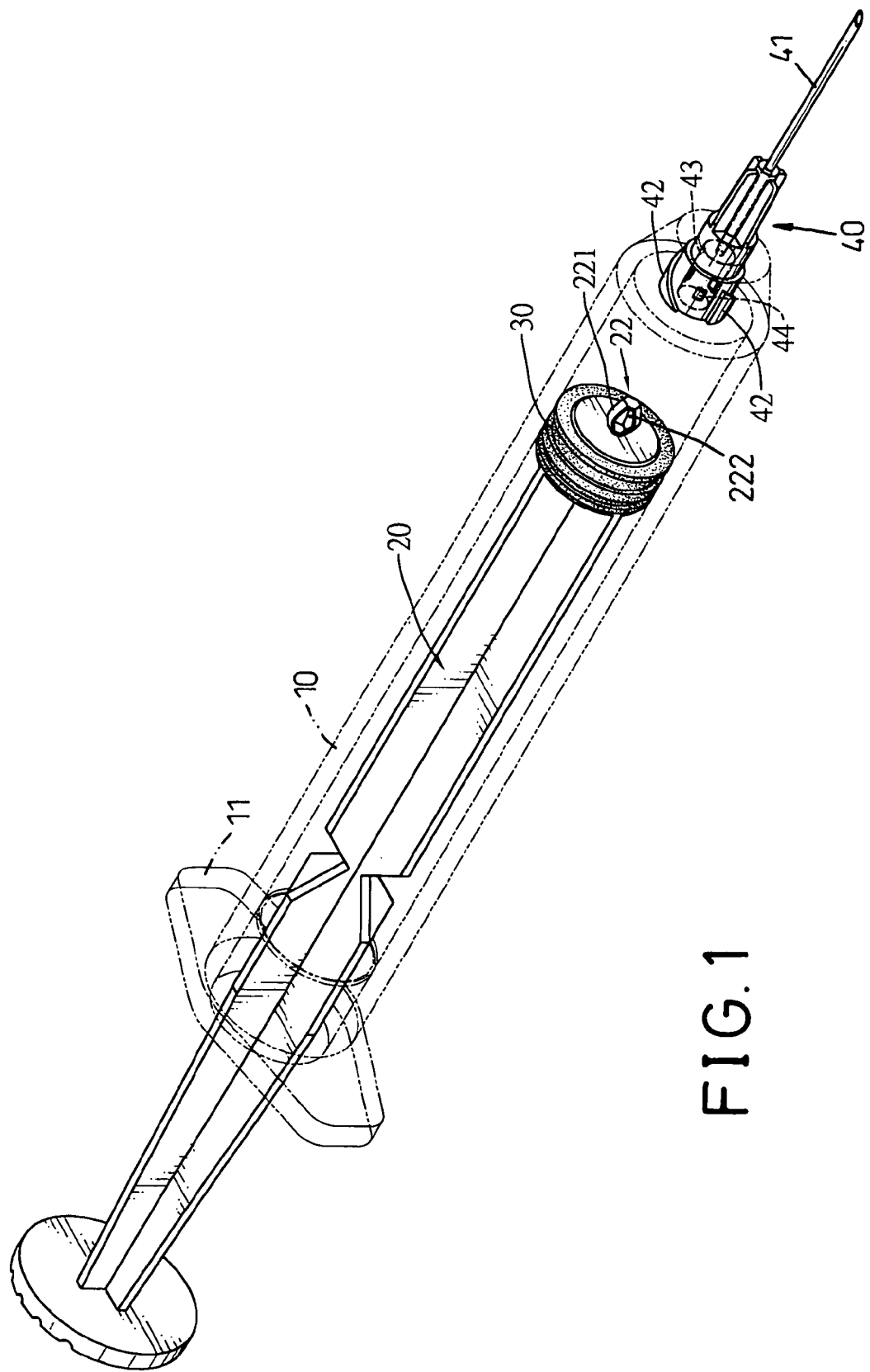
FIG. 1 is a perspective view of a safety syringe in accordance with the present invention.
Figure 2:
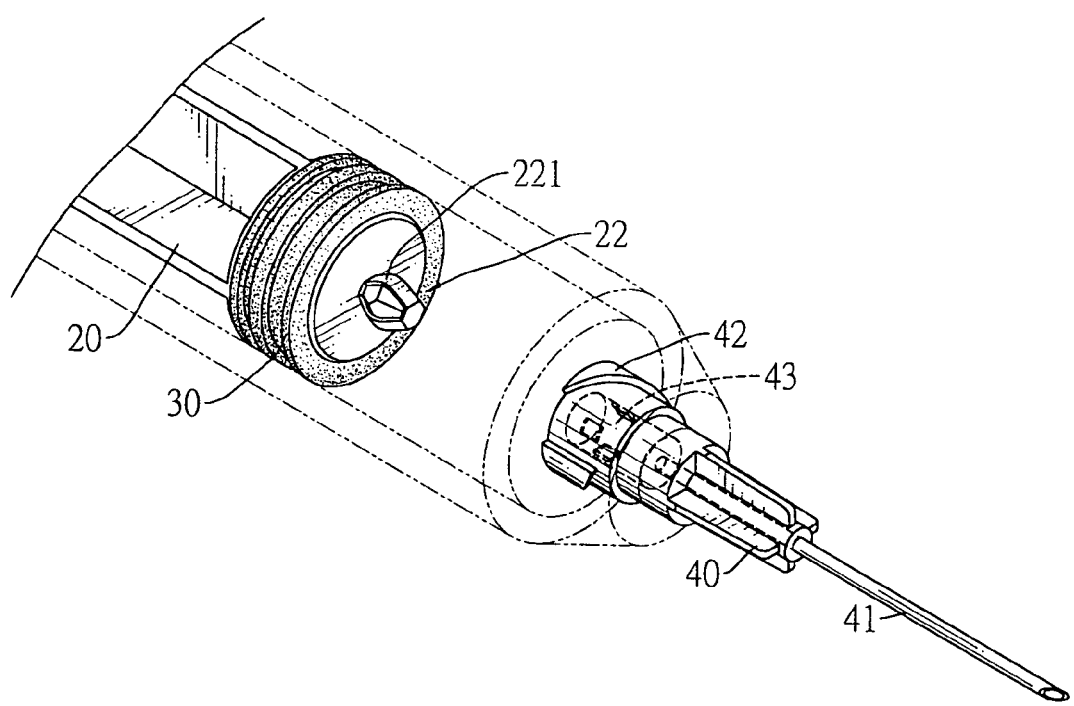
FIG. 2 is an enlarged perspective view of the proximal end of the safety syringe in FIG. 1.
Figure 3:
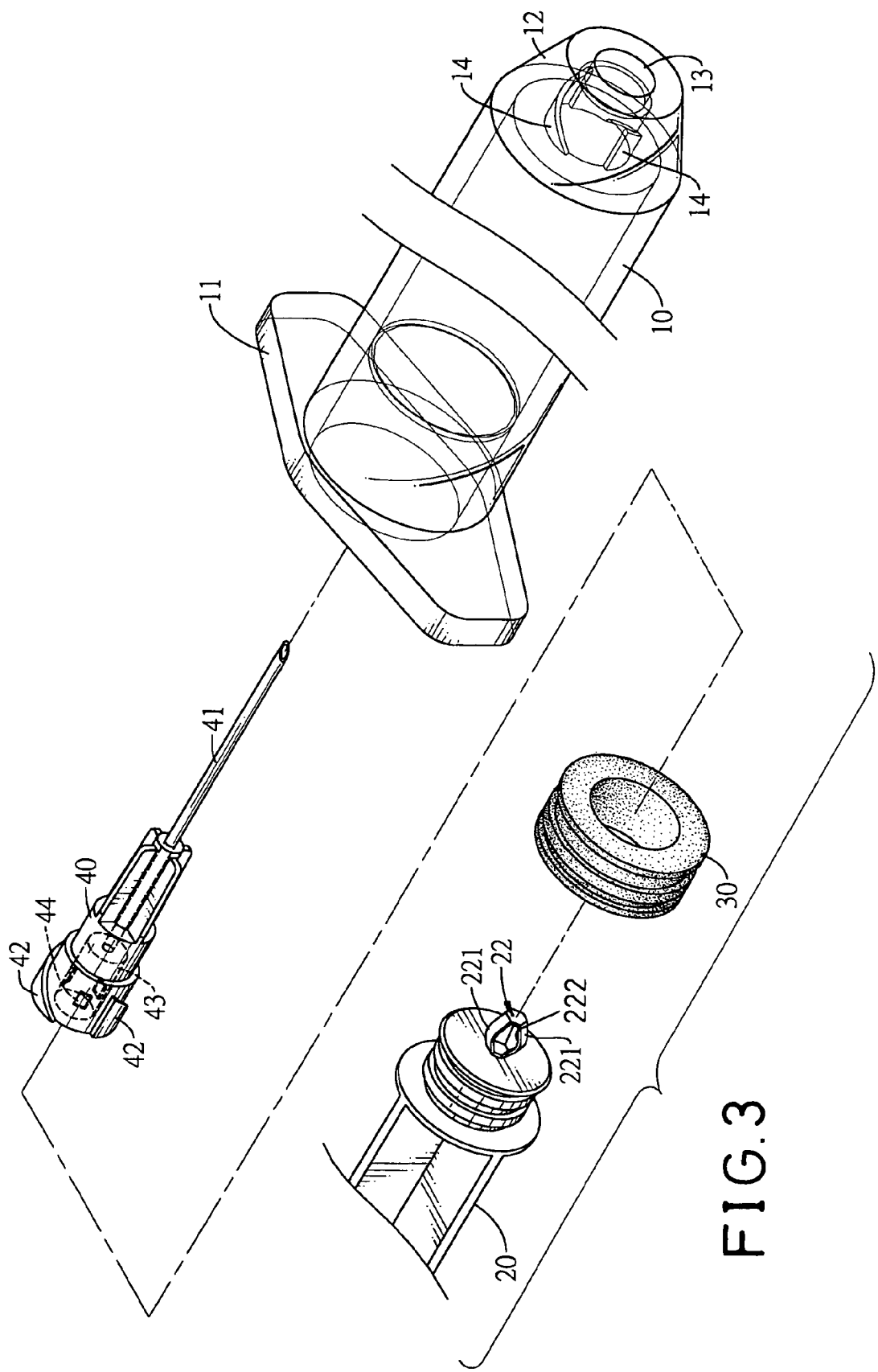
FIG. 3 is an exploded perspective view of the safety syringe in FIG. 2.

With reference to FIGS. 1 to 3, a safety syringe in accordance with the present invention has a hollow barrel (10), a plunger (20), a seal (30) and a needle hub (40) with a needle (41).

The hollow barrel (10) is cylindrical and has a distal end (not numbered), a proximal end (not numbered), a flange (11), a cone-shaped end (12) and two spiral recesses (14). The flange (11) is defined radially around and extends out from the distal end of the hollow barrel (10). The cone-shaped end (12) has an opening (13) and an inner surface (not numbered) and is formed at the proximal end of the hollow barrel (10). The spiral recesses (14) are defined on the inner surface of the cone-shaped end (12).

The seal (30) is made of resilient material, has an axial through hole (not numbered) and is mounted slidably inside the hollow barrel (10).

The plunger (20) has a proximal end (not numbered), a front head (21) and a needle retractor (not numbered) such as an axial protruding lock (22). The front head (21) is integrally formed on the proximal end of the plunger (20) and has a top surface (not numbered). The axial protruding lock (22) is formed on the top surface of the front head (21). The axial protruding lock (22) has multiple resilient pieces (221) and gaps (222) defined respectively between adjacent resilient pieces (221). The seal (30) is mounted around the front head (21), and the axial protruding lock (22) extends out of the through hole in the seal (30).

The needle hub (40) with the needle (41) is mounted detachably inside the cone-shaped end (12) of the hollow barrel (10) so the needle (41) extends out of the opening (13). The needle hub (40) has an outside surface (not numbered), an axial passage (not numbered), an axial locking chamber (43), at least two spiral keys (42) and a latch (not numbered) such as multiple posts (44). The axial passage is defined through the needle hub (40), and one end of the needle (41) is inserted into the axial passage of the needle hub (40). The needle (41) has a fluid passage (not numbered) defined axially through the needle (41). The axial locking chamber (43) has an inside surface (not numbered) and is defined inside the needle hub (40), and the axial passage communicates with the axial locking chamber (43) and the inner space in the hollow barrel (10). The spiral keys (42) are formed on the outside surface of needle hub (40) and engage the spiral recesses (14) in the cone-shaped end of the hollow barrel (10). The posts (44) are formed on the inside surface of the axial locking chamber (43) of the needle hub (40) and holding the axial protruding lock (22). When the plunger (20) is pressed completely into the hollow barrel (10), the axial protruding lock (22) is pressed into the locking chamber (43) in the needle hub (40), and the posts (44) slide respectively into a corresponding gap (222) between adjacent resilient pieces (221) of the axial protruding lock (22).

Figure 6:
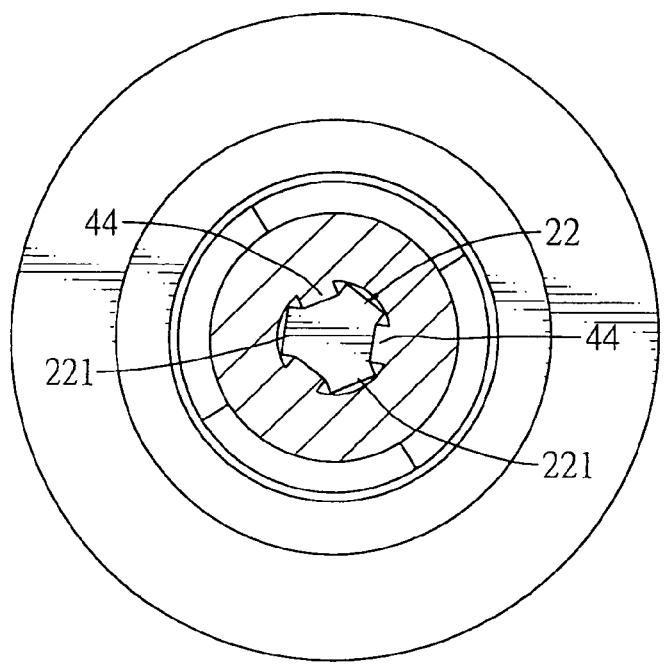
FIG. 6 is an end view in partial section of the safety syringe in FIG. 4 with the needle retractor on the plunger connected to the axial fitting on the needle hub.
Figure 4:
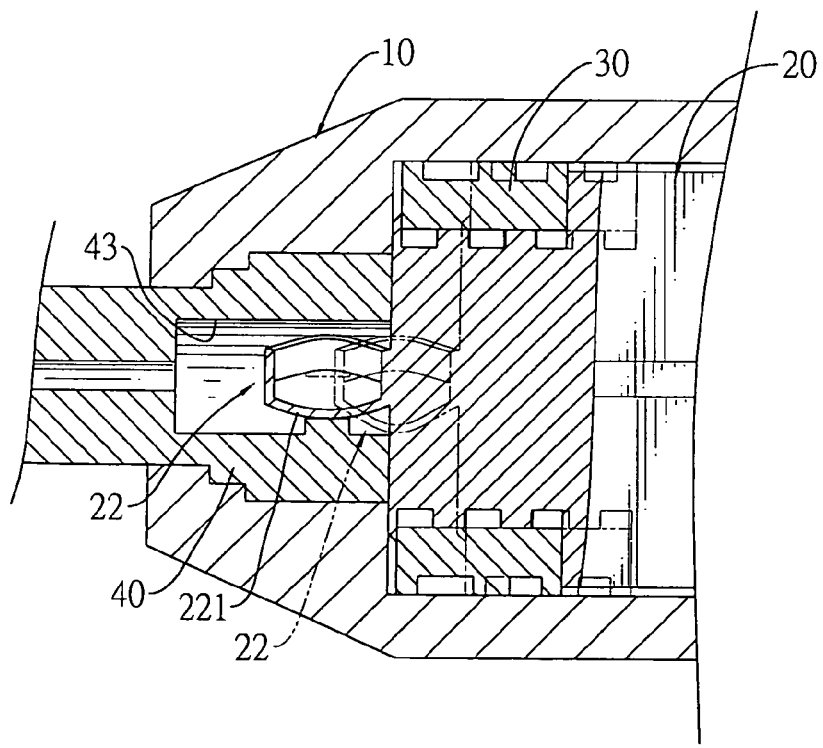
FIG. 4 is an enlarged side plan view in partial section of the needle hub mounted in the safety syringe in FIG. 1.
Figure 5:
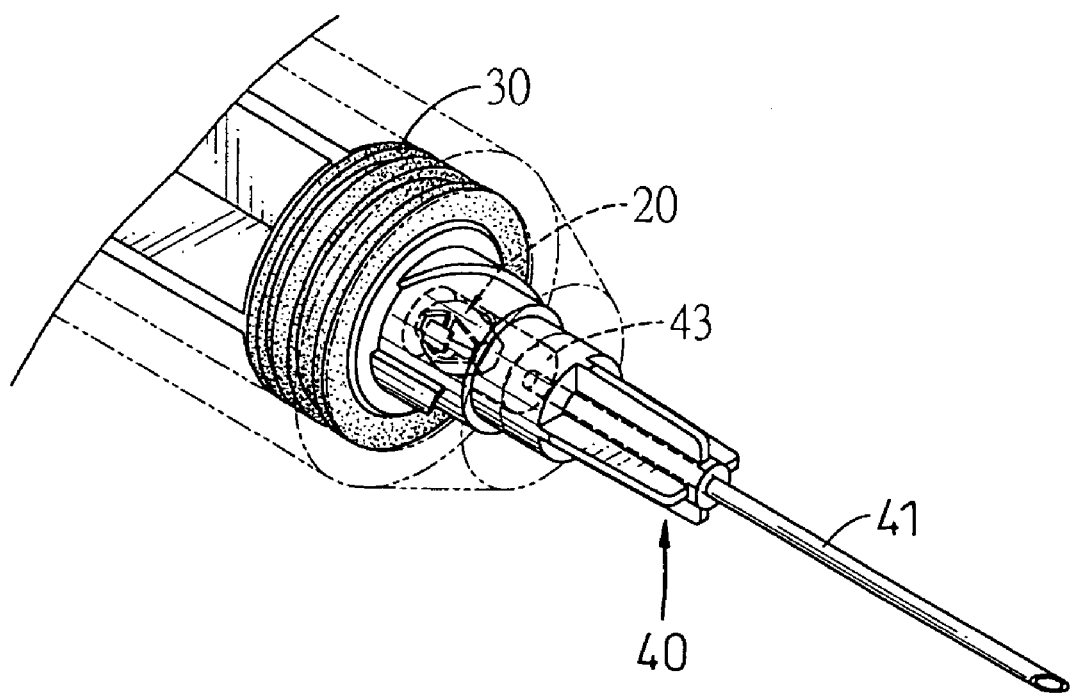
FIG. 5 is an enlarged operational perspective view of the safety syringe in FIG. 2 with the needle retractor on the plunger connected to the axial fitting on the needle hub.

With reference to FIGS. 4 to 6, the safety syringe can be used to draw blood from a body by aligning the resilient pieces (221) of the axial protruding lock (22) with the posts (44) in the locking chamber (43) and pushing the plunger (20) toward the proximal end of the hollow barrel (10). The axial protruding lock (22) is pushed into the axial locking chamber (43) of the needle hub (40), and the resilient pieces (221) are pressed respectively inward by the corresponding posts (44) so the plunger (20) can be pulled away from the proximal end of the hollow barrel (10) again.

Figure 7:
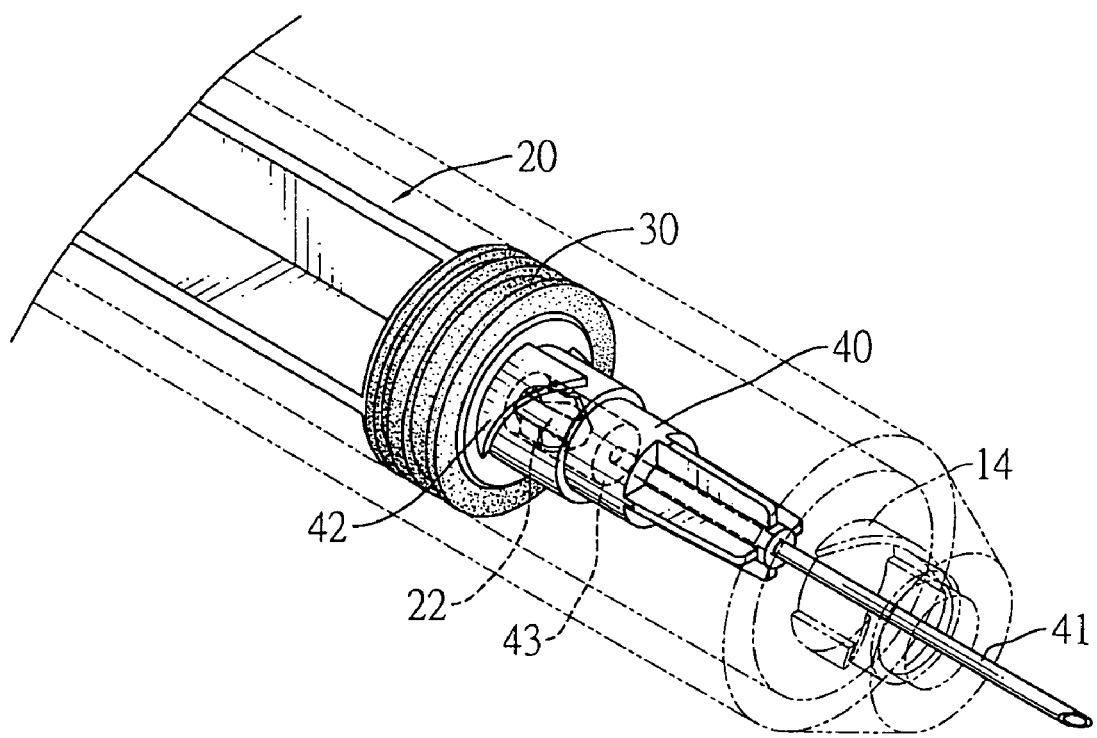
FIG. 7 is a perspective view of the safety syringe in FIG. 1 with the needle being pulled into the hollow barrel.

With reference to FIG. 7, after the needle (21) is inserted into a patient to inject medicine, the plunger (20) is rotated so the gaps (222) between adjacent resilient pieces (221) engage the posts (44) so the plunger (20) securely attaches to the needle hub (40). Rotating the plunger (20) with the needle hub (40), the spiral keys (42) of the needle hub (40) will leave away from the spinal recess (14) of the hollow barrel (10). Then the plunger (20) can be pulled away from the proximal end of the hollow barrel (10), the needle hub (40) and the needle (41) are pulled inside the hollow barrel (10) so the needle (41) cannot injure anyone.

The safety syringe in accordance with the present invention has the following advantages:

1. The plunger (20) is securely connected to the needle hub (40) by the needle retractor engaging the axial fitting. The gaps (222) in the axial protruding lock (22) respectively engage the posts (44) to prevent the plunger (20) from pulling away from the needle hub (40) when the needle (41) is pulled into the hollow barrel (10).
2. Rotating the plunger (20) to engage the needle hub (40) is easier than techniques used to connect the conventional ones, and the axial protruding lock (22) can be used with various sizes of the axial locking chambers (43).

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A safety syringe comprising:
   (a) a hollow barrel being cylindrical and comprising:
      a distal end;
      a proximal end;
      a flange formed radially around and extending out from the distal end;
      a cone-shaped end integrally formed at the proximal end of the hollow barrel, said cone-shaped end having an opening defined therethrough; an inner surface, and an at least one spiral recess formed on the inner surface of the cone-shaped end;
   (b) a plunger comprising:
      a distal end;
      a proximal end;
      a front head integrally formed on the proximal end of the plunger and having a top surface;
   (c) a unitary axially protruding needle retractor lock;
   said plunger being connected to said seal member fixedly seated on said plunger, with the seal having a substantially circular cross-sectional profile and an outer diameter substantially equal to an inner cross-sectional diameter of said hollow barrel, telescopingly received and slidingly contiguous with said inner surface of said hollow barrel; and,
   (d) a needle assembly comprising:
      a needle hub having a needle and being detachably mounted inside the proximal open end of the hollow barrel, said needle hub comprising:
      an outer surface;
         an at least one spiral key formed on the outside surface and received inside the spiral recess of the hollow barrel when the needle hub is mounted inside the cone-shaped end of the hollow barrel, said needle assembly being rotatably connectable to said at least one spiral recess at the cone-shaped end of the hollow barrel;
      a locking chamber axially positioned and formed within said needle assembly and having an inner surface;
      an at least one latch lug post fixedly formed on the inner surface of the axial locking chamber and extending radially inward;
   a fluid passage communicating with the inner space in the hollow barrel; and
   an axial passage defined through the needle hub to receive an end of the needle, wherein rotating the plunger connectedly engages the needle assembly and hub with the needle retractor of the plunger, said needle retractor formed as a closed contour resilient element having at least one gap recess formed therein and formed axially on and protruding longitudinally from the top surface of the front head of said plunger, said closed contour resilient element being insertable into the locking chamber of hub, wherein upon a rotation of said closed contour resilient element said lug post member is received into said gap recess to capture said needle assembly by the needle retractor of said plunger, whereby said needle assembly may be axially moved into said hollow barrel.

2. The safety syringe as claimed in claim 1, wherein the needle retractor of the plunger is an axial protruding lock, with the latch of the needle hub comprised of lug post members engagable by the gap recesses upon the rotation of the plunger.

* * * * *